(12) United States Patent
Bernard et al.

(10) Patent No.: US 8,845,182 B2
(45) Date of Patent: Sep. 30, 2014

(54) VESSEL FOR PROCESSING A BIOPHARMACEUTICAL PRODUCT INCLUDING PROTECTION MEANS

(75) Inventors: Frederic Bernard, La Cadiere d'Azur (FR); Eric Chevalier, Paris (FR)

(73) Assignee: Sartorius Stedim FMT SAS, Aubagne (FR)

( * ) Notice: Subject to any disclaimer, the term of this patent is extended or adjusted under 35 U.S.C. 154(b) by 1121 days.

(21) Appl. No.: 12/681,419

(22) PCT Filed: Oct. 1, 2008

(86) PCT No.: PCT/FR2008/051768
§ 371 (c)(1),
(2), (4) Date: May 7, 2010

(87) PCT Pub. No.: WO2009/053572
PCT Pub. Date: Apr. 30, 2009

(65) Prior Publication Data
US 2010/0220547 A1 Sep. 2, 2010

(30) Foreign Application Priority Data
Oct. 4, 2007 (FR) ...................................... 07 06974

(51) Int. Cl.
*B01F 7/16* (2006.01)
*B65D 30/20* (2006.01)

(52) U.S. Cl.
USPC .......................... 366/314; 206/219; 604/903

(58) Field of Classification Search
USPC .......................... 366/273–274, 348, 349, 314;
435/302.1; 383/127; 416/3;
206/219–221, 818; 215/DIG. 3, DIG. 8;
604/416, 903
See application file for complete search history.

(56) References Cited

U.S. PATENT DOCUMENTS

| 3,647,397 | A | * | 3/1972 | Coleman .................... 366/167.1 |
| 5,350,080 | A | * | 9/1994 | Brown et al. ............... 220/62.21 |
| 5,533,804 | A | * | 7/1996 | Larsson et al. ................ 366/274 |
| 5,803,137 | A | * | 9/1998 | Shimotoyodome et al. .... 141/67 |
| 5,941,635 | A | * | 8/1999 | Stewart ...................... 366/165.5 |

(Continued)

FOREIGN PATENT DOCUMENTS

| GB | 2 080 756 A | 2/1982 |
| WO | 00/04131 A1 | 1/2000 |
| WO | 2008/040569 A1 * | 4/2008 |

OTHER PUBLICATIONS

International Search Report, dated Apr. 22, 2009, from corresponding PCT application.

*Primary Examiner* — Charles Cooley
(74) *Attorney, Agent, or Firm* — Young & Thompson

(57) ABSTRACT

A vessel includes: a pocket capable of assuming a folded state and an expanded state, processing element including an active inner portion; protection element including a side wall, a lower portion and an upper portion defining an inner space, the lower portion being attached to the upper portion of the pocket, the active inner portion being provided in the inner space when the pocket is in the folded state, the peripheral portion of the inner space about the processing element defining a protection chamber; at least one insertion and/or draining opening. The active inner portion is provided inside the pocket adjacent to the lower end portion thereof, the processing element and the protection element are independent in terms of their movements, and the height of the protection chamber is variable and automatically adapts itself based on respectively, the flat-folded, unfolded and expanded states or any intermediate state of the pocket.

22 Claims, 4 Drawing Sheets

(56) References Cited

U.S. PATENT DOCUMENTS

| | | | |
|---|---|---|---|
| 5,988,422 A | 11/1999 | Vallot | |
| 6,844,186 B2* | 1/2005 | Carll | 435/289.1 |
| 7,153,021 B2* | 12/2006 | Goodwin et al. | 366/273 |
| 7,278,780 B2* | 10/2007 | Goodwin et al. | 366/273 |
| 7,695,186 B2* | 4/2010 | Terentiev | 366/279 |
| 8,282,267 B2* | 10/2012 | Castillo et al. | 366/262 |
| 8,292,491 B2* | 10/2012 | Castillo et al. | 366/273 |
| 2004/0190372 A1* | 9/2004 | Goodwin et al. | 366/273 |
| 2004/0245144 A1* | 12/2004 | Hurst | 206/527 |
| 2006/0176772 A1* | 8/2006 | Goodwin et al. | 366/273 |
| 2007/0224676 A1 | 9/2007 | Haq | |
| 2007/0253287 A1* | 11/2007 | Myhrberg et al. | 366/273 |
| 2010/0220547 A1* | 9/2010 | Bernard et al. | 366/150.1 |
| 2011/0013474 A1* | 1/2011 | Ludwig et al. | 366/102 |
| 2011/0158037 A1* | 6/2011 | Bernard et al. | 366/173.2 |
| 2012/0027324 A1* | 2/2012 | Morrissey et al. | 383/105 |
| 2012/0155216 A1* | 6/2012 | Morrissey et al. | 366/273 |

\* cited by examiner

VESSEL FOR PROCESSING A BIOPHARMACEUTICAL PRODUCT INCLUDING PROTECTION MEANS

FIELD OF THE INVENTION

The invention relates to a biopharmaceutical product processing receptacle. Its object is more particularly such a receptacle, a processing device that incorporates such a receptacle, and the process for using such a receptacle.

"Biopharmaceutical product" is defined here as one (or more) product(s) obtained from biotechnology—culture media, cellular cultures, buffer solutions, artificial nutrition liquids, blood products, and derivatives of blood products—or a pharmaceutical product, or more generally a product that is designed to be used in the medical field. Such a product is in liquid, pasty or powder form, in one or more phases, homogeneous or not. The invention also applies to products other than biopharmaceutical products, according to the definition that was just given, but that are subject to analogous requirements relative to their processing.

BACKGROUND OF THE INVENTION

A pocket is known that is designed to accommodate such a biopharmaceutical product, which comprises a lower end wall, an upper end wall, and, between them, a flexible side wall that can be—in line with the pocket itself—in two extreme states—a flat-folded state, and an expanded, unfolded state—and can be deformed to switch from one of these extreme states to the other or be in any intermediate state. The walls of the pocket, made of plastic such as polyethylene or a complex that comprises polyethylene, define an inner space that, in the folded state, has a minimum and even zero or almost-zero volume, and, in the unfolded and expanded state, has a maximum volume. This space is designed to accommodate the biopharmaceutical product.

Such a pocket is designed either for simple storage of the biopharmaceutical product or for specific processing, i.e., any action on the product or relative to this product and involving contact with the product, such as mixing, aeration, filtration, and measurement, whereby this list is not exhaustive. For this purpose, such a processing means that is suitable for the desired action, such as a mixing propeller, aerator, filter, or probe is implemented, whereby this list is not exhaustive. Such a (or such) processing means is (are), at least in part, placed actually inside the pocket by being adjacent to its lower portion (on it, close to it, or in its vicinity), so as to be able to be in contact with the product.

The preceding constructive arrangements are not without risk. Actually, when the pocket is in the flat-folded state or in a slightly unfolded or nearly folded state or switches from one of these states to the other, there is a risk that the active inner portion of the processing means will interfere with the wall of the pocket, more particularly the wall of the upper end, and more or less significantly alter its integrity and its qualities by embrittling it, perforating it or tearing it. Furthermore, there is also a risk that the active inner portion of the processing means will interfere with exogenic elements that are outside of the pocket (such as supports or other devices that are next to the pocket) and be more or less significantly altered, for example deformed or moved or else wedged.

These constructive arrangements exhibit another drawback, namely not allowing complete draining of the contents of the pocket. Actually, the pocket under the action of the reduction of pressure resulting from draining flattens against the active inner portion of the processing means with a serious risk of tearing, most often compensated for by not draining the pocket completely.

The document WO 00/04131 describes a pocket with gussets having a side portion, an upper portion, and a lower portion, designed to contain one (or more) such biopharmaceutical product(s), with a volume of 50 liters and more. Such a pocket can be found either in a flat-folded state for being stored empty or in an unfolded and expanded state where it has a general pallelepipedic shape when it contains a product. According to the embodiments, such a pocket also comprises, in the upper portion, one (or several) opening(s) or connection(s) designed to allow its filling and, in the lower portion, an outlet that is designed to allow it to drain.

The document U.S. Pat. No. 5,350,080 describes a system that comprises a rigid outer container that supports a pocket that defines an inner storage chamber whose access is possible through a filling port that is located in the upper portion and a draining port that can be provided in the lower portion. When the contents of the pocket are drained, the upper filling port is forced by its own weight toward the lower portion of the pocket. In the case where the inner portion of the filling port has no tube, it can come into contact with the lower portion of the pocket, where there is the risk that it may become damaged and locked. Also, it is provided that the filling port comprises a side skirt whose height is greater than the length of the downward projection of the inner portion of the filling port, such that this inner portion is housed entirely within the skirt and its lower end is always located above the lower portion of the pocket, even when the skirt rests on the latter.

The documents US 2007/0224676 and GB 2 080 756 describe receptacles that comprise an accordion-like flexible side wall, capable of being folded or unfolded, and, on both sides of the latter, two end walls, respectively, lower and upper, whereby the latter is provided with an opening.

SUMMARY OF THE INVENTION

The object of the invention is to eliminate the above-mentioned drawbacks that are linked to the presence of processing means arranged in foldable pockets that can be arranged flat-folded.

For this purpose, and according to a first aspect, the object of the invention is a processing receptacle for at least one biopharmaceutical product, comprising:
  A pocket that has a flexible side wall, a lower end portion, and an upper end portion that define an inner space that is designed to accommodate at least one product that can be in two extreme states, flat-folded and expanded, and in any intermediate state, and can be deformed to switch from one state to the other;
  Means for processing at least one product that is contained in the receiving space of the pocket, comprising an inner portion of a certain height that is arranged inside the receptacle;
  Protective means of the processing means, comprising a side wall, a lower end portion and an upper end portion that define an inner space communicating with the inner space of the pocket, whose lower end portion is adjacent and attached rigidly to the upper end portion of the pocket, the movement of the latter upward or downward bringing about a movement of the protective means, whereby the inner portion of the processing means is essentially arranged in the inner space of the protective means when the pocket is in the flat-folded state, the peripheral portion of the inner space of the protective means around processing means forming a protective chamber of the pocket and processing means;

At least one opening for introducing at least one product into the receptacle and/or for draining the contents from the receptacle;

in which:

The processing means are at least partially—mixing element, sensor, tube, aerating element, etc.—arranged inside the pocket by being adjacent to its lower end portion;

The processing means and the protective means are arranged to be independent from one another relative to their movements;

The variable height of the protective chamber can be one of two extreme heights, maximum and minimum, and any intermediate height, and can be adapted automatically, based on the state that is respectively flat-folded, unfolded and expanded, and any intermediate state of the pocket;

such that in each state of the pocket, the processing means are offset from the side wall and the upper end portion of the pocket, while being adjacent to its lower end portion.

In a first embodiment, the protective means are rigid and non-deformable. In a second embodiment, the protective means are deformable in height, whereby the side wall comprises at least one deformable section between two extreme states, respectively folded and expanded, capable of being deformed to switch from one state to the other, whereby the receptacle also comprises means that are capable of keeping the deformable section expanded, at least in the flat-folded extreme state of the pocket. In this second embodiment, these means that are capable of keeping the deformable section expanded, at least in the flat-folded extreme state of the pocket, are either integrated in the side wall of the protective means or separate from it.

According to one embodiment, the protective means are arranged to form a head for introducing at least one product into the receptacle. In this case, the protective means that form an introduction head comprise at least one opening for introducing said at least one product that is provided in the upper end portion of the protective means and removable sealing means of said opening that are capable of ensuring its closing and its opening, such as a plug or a membrane. In addition, the introduction head can, in one embodiment, comprise means for removable connection of the receptacle to an aseptic transfer device.

According to one embodiment, at least one opening is provided in the receptacle for introducing at least one product and/or for draining the contents, provided in the pocket, from the receptacle, in particular in the lower end portion.

According to one embodiment, a pocket that is equipped on the inside with a rigid plate is provided on its lower end portion.

According to one characteristic, the protective means ensure in combination the protective function of the pocket and processing means and a guiding function of the pocket when, the filling opening of the receptacle being open, at least one product is gradually introduced into the receptacle, whereas the pocket simultaneously expands upward.

According to one embodiment, the processing means and the protective means are dissociated structurally from one another, being separate from one another and without direct contact with one another, whereby the peripheral portion of the inner space of the protective means around processing means form a protective chamber that extends laterally and on the top between the processing means and the side wall and the upper end portion of the protective means.

According to one embodiment, the processing means have a portion inside the pocket that, in the flat-folded state of the pocket, essentially occupies the inner space of the protective means. According to one embodiment, the processing means have a portion inside the pocket that, in the expanded state of the pocket, is essentially integral within the inner space of the pocket, the height, minimum here, of the protective chamber being zero.

According to one embodiment, the processing means have a portion inside the carried pocket, if necessary with the possibility of relative movement, by the inside surface of the lower end portion of the pocket or by a rigid plate with which the lower end portion of the pocket is equipped on the inside.

According to one characteristic, the receptacle comprises means that are capable of participating in its preservation in a container, whereby the pocket contains the desired amount of at least one product. According to one embodiment, such means are integrated or combined with protective means.

According to a particular embodiment, the processing means are mixing means, whereby the receptacle comprises at least a first introduction opening in the receptacle of a first portion of at least one product that is made on the pocket, in particular adjacent to its lower end portion, and at least a second introduction opening of a second portion of at least one product that is provided in the upper end portion of the protective means. The receptacle is then a mixing receptacle.

According to a second aspect, the object of the invention is a device for processing at least one biopharmaceutical product that comprises a receptacle as was just described and a rigid container that is capable of accommodating the receptacle whose pocket is in the flat-folded state, in the expanded state, or in an intermediate state, and capable of allowing the pocket to be deformed to switch from one state to the other, and of guiding the pocket, in particular its flexible side wall, so that the pocket is expanded in volume by having an additional volume of that of the container, when the at least one product is introduced into the receptacle.

According to another aspect, the object of the invention is a process for the implementation of such a processing device, in which:

There are a receptacle and a container that constitute the processing device, and the pocket of the receptacle is placed in the flat-folded state in the bottom of the container;

An opening for introducing a product from the receptacle being open, the at least one product is gradually introduced into the receptacle and simultaneously the pocket is allowed to expand upward and to be expanded in volume by the container, the inner space of the pocket, of increasing volume, accommodating at least one product; this stage is continued until having introduced into the container the desired amount of at least one product;

During this stage, the protective means are allowed to move upward, being entrained by the movement of the upper end portion of the pocket;

During this stage, the height of the protective chamber is allowed to decrease starting from the maximum extreme height and automatically adapts based on the state of the pocket until the pocket is in the unfolded and expanded state or any intermediate state based on the amount of product that is introduced into the receptacle, such that in all the states of the pocket, the processing means are offset from the side wall and the upper end portion of the pocket, while being adjacent to is lower end portion;

The processing means of at least one product that is in the receptacle are implemented.

According to the embodiments, the implementation of the processing means of at least one product that is in the receptacle is begun before, at the time of, or after the introduction of the desired amount of at least one product into the receptacle.

According to a particular application with mixing:
There is a mixing receptacle of which at least the second opening is sealed;
The pocket of the receptacle is placed in the flat-folded state in the bottom of the container;
A first portion of at least one product is introduced into the mixing receptacle via at least a first introduction opening that is open for this purpose;
And a second portion of at least one product is introduced into the receptacle by at least a second introduction opening that is open for this purpose.

According to the embodiments of this mixing process, the mixing means are implemented while at least a second introduction opening is open or closed.

According to one embodiment, made possible by the invention, the mixing means are implemented until the pocket is completely or essentially completely drained.

BRIEF DESCRIPTION OF THE DRAWINGS

Several embodiments of the invention are now described using drawings, in which.

DETAILED DESCRIPTION OF THE INVENTION

Figure 1:
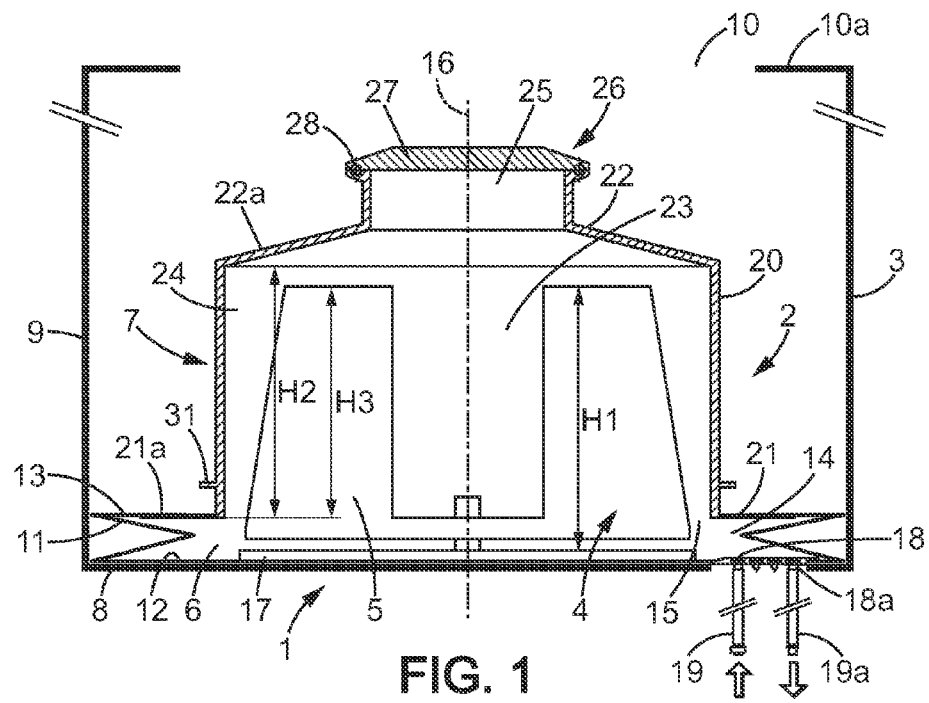
FIG. 1 is a diagrammatic axial cutaway view of a first embodiment of a processing device—here a mixing device—that has a receptacle with rigid and non-deformable protective means, whereby the mixing receptacle, whose pocket is in the flat-folded extreme state, comprises a head for introducing at least one product that has an opening and sealing means that close the receptacle.

A device 1 for processing at least one biopharmaceutical product comprises a processing receptacle 2 and a rigid container 3 that is capable of accommodating the receptacle 2 in a removable manner.

As indicated above, "biopharmaceutical product" is defined as one (or more) product(s) obtained from biotechnology—culture media, cellular cultures, buffer solutions, artificial nutrition liquids, blood products and derivatives of blood products—or a pharmaceutical product or more generally a product that is designed to be used in the medical field.

Such a product is in liquid, pasty or powder form, in one or more phases, homogeneous or not.

Of course, the invention also applies to products other than biopharmaceutical products, according to the definition that was just given, but which is subject to analogous requirements relative to their processing.

As indicated above, "processing" is defined as any action on the biopharmaceutical product or that relates to this product and that involves a contact with the product.

In the particular embodiment that is described below, such a processing is mixing.

In other embodiments, the processing is aeration, filtration, and measurement, whereby this list is not exhaustive.

In any case, processing means 4 that are appropriate for the desired action are implemented.

For example, the means 4 comprise an inner active portion 5, rigid within its unit, and, as appropriate, deformable or not. Such an inner active portion 5 is, for example, a propeller in the case of mixing, an aerator in the case of aeration, a filter in the case of filtration, and a probe in the case of measuring, whereby this list is furthermore not exhaustive.

In the case where the processing is the measuring, the latter is done for various purposes: monitoring of such a parameter that relates to the biopharmaceutical product, control of the processing, . . . .

The receptacle 2 comprises, in addition to the processing means 4, a pocket 6 and protective means 7 that ensure a first protective function of the pocket 6 and processing means 4.

In the embodiment that is shown and described, the container 3 has a general parallelepipedic shape, in particular cubic or approximately cubic, having a bottom 8, a side wall 9 that comprises four panels and an opening 10 that is opposite to the bottom 8, limited by a collar return 10a of the side wall 9. It is understood that the container 3 can have another shape, if necessary.

In the standard position in which the container 3 can be used, the bottom 8 extends horizontally in the lower portion; the side wall 9 extends vertically, and the opening 10 is placed in the upper portion at the base of the bottom 8. In contrast, the side wall 9 can comprise an access door and the bottom 8 and/or the side wall of the openings or passages of devices that are connected to the receptacle 2 such as connections.

The words "horizontal," "lower," "vertical," "upper," like the words "height," "top," and "bottom," refer to the processing device 1, to the receptacle 2, and to the container 3 that are in their standard position in which they can be used. Nevertheless, it is well understood that they can be placed in another position, in other circumstances.

It is also understood that the words "horizontal" and "vertical" pertain to both the respective exactly horizontal and vertical positions and those that are approximately so, without it being necessary to so specify expressly.

The pocket 6 is now described more particularly.

The pocket 6 comprises a flexible side wall 11, a flat lower end portion 12, and an upper end portion 13 that delimits an inner space 14 that is designed to accommodate the at least one product.

When, in the container 3, the pocket 6 is expanded and expanded in volume, it has, in the embodiment shown and described, a general parallelepipedic shape, in particular cubic or approximately cubic, like the container 3, with a side wall 11 that is arranged vertically, a lower end part 12 that is arranged horizontally and an upper end part 13 that is itself also arranged horizontally or more or less inclined in the form of a roof. It is understood that the pocket 6 can have another shape, if necessary, corresponding to that of the container 3.

The upper end portion 13 comprises one or more passages or openings 15. In the embodiment that is shown and described, a single passage 15 that is located in the median portion of the upper end portion 13, which has a general collar or ring shape, is provided.

Such a pocket 6 can have a volume that exceeds 50 l and can reach 3,000 l. It can have a length, a width, and a height, according to the volume, of between about 30 and close to 150 centimeters.

In one embodiment, the side wall 11, the lower end portion 12, and the upper end portion 13 of the pocket 6 are produced integrally and entirely of plastic, starting from a rather thin sheet material in order to have the required flexibility. This material is selected based on the contents that the pocket is designed to accommodate, and, in particular, it is biocompatible with the biopharmaceutical products that are received, capable of sterilization and impermeable to gases.

Typically, the constituent material of the pocket 6 is such that the pocket 6 is able to be embrittled, perforated or torn in the case of interference with something rigid that has angles, corners, points, or sharp edges, which can be the case of the rigid active inner portion 5 of the processing means 4.

Symmetrically, this rigid active inner portion 5, if it comprises angles, corners, points, or sharp edges, can be altered more or less significantly, for example deformed or moved or else wedged, in the case of interference with something rigid or in the case of an impact, whereby the constituent material of the pocket 6 is not capable by itself of protecting it adequately.

Figure 2:
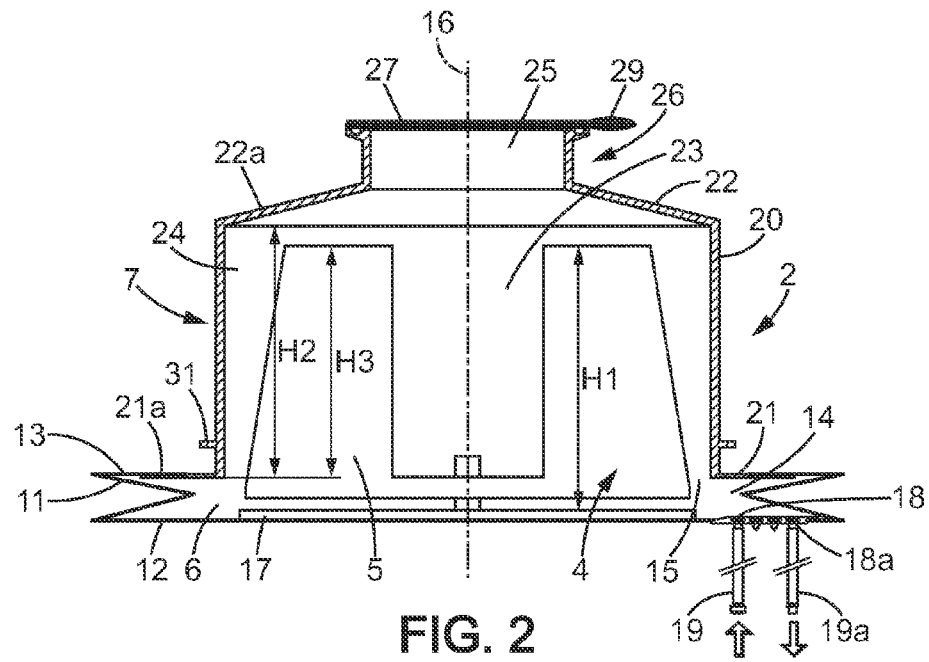
FIG. 2 is a diagrammatic axial cutaway view of the mixing receptacle of FIG. 1 that is provided with other sealing means.
Figure 3:
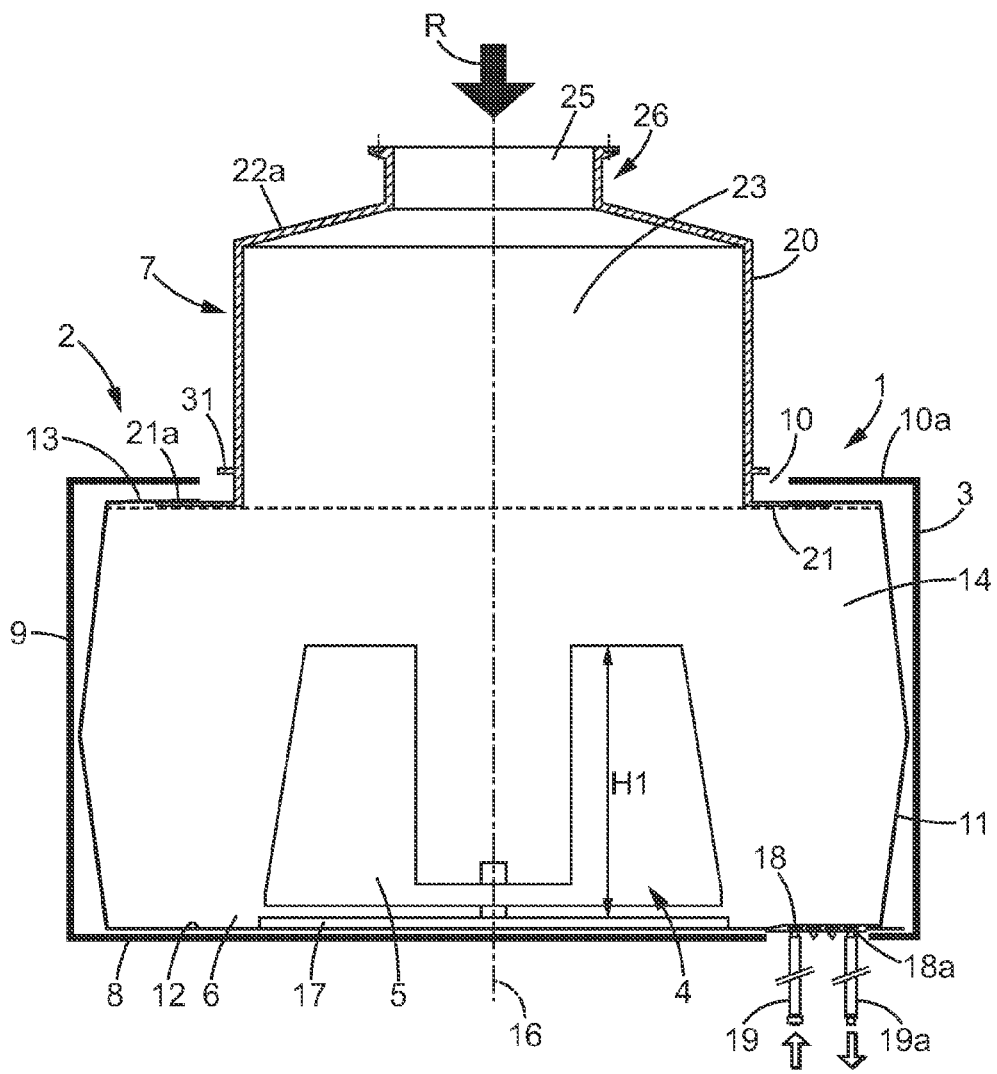
FIG. 3 is a diagrammatic axial cutaway view of the mixing device of FIG. 1, whereby the pocket is in the expanded extreme state.
Figure 4:
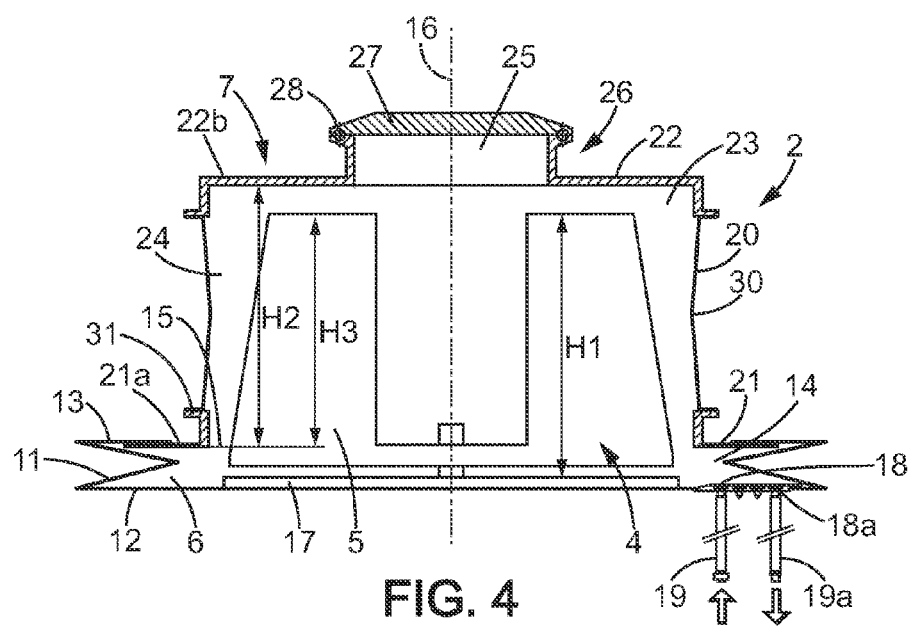
FIG. 4 is a diagrammatic axial cutaway view of a second embodiment of the receptacle, with deformable protective means, whereby the processing receptacle—here a mixing receptacle—whose pocket is in the flat-folded extreme state, comprises a head for introducing at least one product, having an opening and sealing means that close the receptacle.
Figure 5:
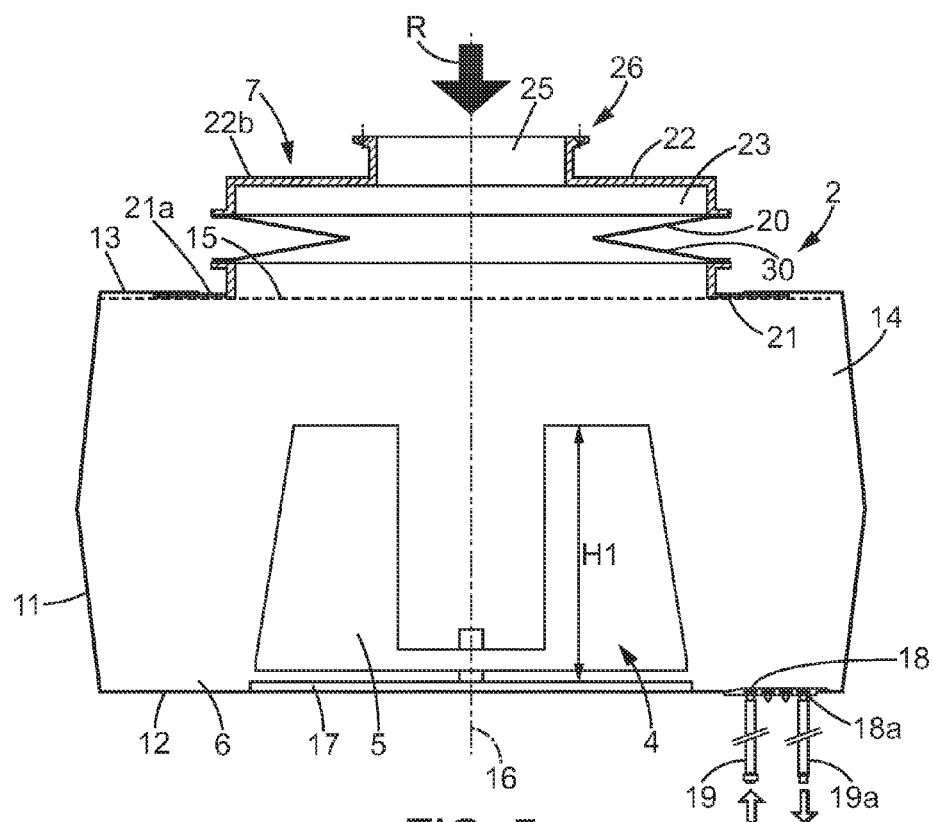
FIG. 5 is a diagrammatic axial cutaway view of the receptacle of FIG. 4, whereby the pocket is in the expanded extreme state.

The flexible side wall 11 is such that the pocket 6 can be in two extreme states, namely a flat-folded state (FIGS. 1, 2 and 4), and an expanded state (FIGS. 3 and 5). The pocket 6 can also be found in any intermediate state between the two extreme states, namely partially expanded. Further, the pocket 6, more particularly the side wall 11, can be deformed for switching from one state to the other, in particular when it is filled or when it is drained.

Analogous states of the receptacle 2 that incorporates the pocket 6 correspond to the folded, expanded, and intermediate states of the pocket 6.

In the folded state, the side wall 11 is folded on itself in a more or less uniform manner like an accordion, whereby the upper end portion 13 rests on or is located in the immediate vicinity of the lower end portion 12, which is flat. The inner space 14 then has minimum volume, even zero or almost zero.

In the expanded state, the side wall 11 extends vertically in a prismatic or cylindrical manner, whereby the upper end portion 13 is offset in height relative to the lower end portion 12, which is flat. The inner space 14 then has maximum volume.

The flexibility of the side wall 11 is such that in the absence of stress, in particular due to the presence of contents in the pocket 6, itself placed in the container 3, the pocket 6 is in the folded state or tends toward this state.

The pocket 6, more generally the device 1, has a vertical axis 16, around which the side wall 11 is located and perpendicular to which the lower end portion 12 is arranged.

The height in question is counted along the axis 16.

In the embodiment that is shown and described, a rigid plate 17 that is arranged in the pocket 6 on the inner surface of its lower end portion 12 is provided.

In the embodiment that is shown and described, a first opening 18 for introducing a first portion of at least one product that is to be mixed into the pocket 6 (and therefore the receptacle 2) is provided on the pocket 6.

This first opening 18 is adjacent to the lower end portion 12, for example more or less laterally. If a rigid plate 17 is provided, and if the opening 18 is opposite the latter, the opening 18 is also provided in the rigid plate 17.

Structurally and functionally, an intake pipe 19 of the first portion of at least one product that is to be mixed can be connected to the opening 18, forming part of the intake means (pump, for example).

Of course, there can be provided not one, but several openings 18.

Further, at least one opening 18a for draining the contents from the pocket 6 (and therefore from the receptacle 2) is provided. This draining opening is itself adjacent to the lower end portion 12. It may or may not be in common with the opening 18 and be connected to a drainpipe 19a, which may or may not be the intake pipe 19, forming part of the draining means.

The processing means 4, in the type of mixing, will now be described more particularly in the embodiment that is shown and described.

As indicated, the means 4 comprise an inner active portion 5, rigid in its entirety and, as appropriate, deformable or not. This inner active portion 5 has a certain height H1 that is counted along the axis 16. It is arranged inside the receptacle 2. More specifically, the inner active portion 5 is adjacent to the lower end portion 12 of the pocket 6. "Adjacent" is defined as the fact that the inner active portion 5 is on (in contact with) the inner surface of the lower end portion 12, the upper inner surface of the rigid plate 17, or close to or in the vicinity of this portion 12 or plate 17. Thus, the inner active portion 5 is in contact with the contents of the pocket, even in a small amount.

According to a possible, but non-limiting embodiment, the inner active portion 5 is connected structurally to the lower end portion 12 or the rigid plate 17, for example by means of a pivoting assembly. Other arrangements are possible.

The means 4 generally comprise other elements and devices, such as engines, control . . . arranged outside of the pocket 6 and the receptacle 2.

The protective means 7, in the embodiment shown (processing that consists of a mixing), are now described more particularly.

The protective means 7, made of plastic, comprise a side wall 20, a lower end portion 21, and an upper end portion 22 that define an inner space 23 that is useful for the housing of the active inner portion 5 of the processing means 4, of height H2.

The inner space 23 of the protective means 7 is in communication with the inner space 14 of the pocket 6 by means of the passage 15 that is common to the pocket 6 and to the means 7. The lower end portion 21 of the means 7 is adjacent and secured rigidly to the upper end portion 13 of the pocket 6, at the periphery of the passage 15, for example by welding, at 21a.

In the embodiment that is shown and described, the side wall 20 is arranged for extending in the vertical direction. The lower end portion 21 forms a collar that extends in a horizontal plane around and outside of the side wall 20, so as to be able to be connected rigidly and in a sealed manner to the upper end portion 13 in collar form of the pocket 6.

As for the upper end portion 22, it comprises—in the embodiment of FIGS. 1 to 3—a tapered section 22a, connected downward at the upper end of the side wall 20 and upward to a portion that forms a port, which will be referenced again below. In the embodiment of FIGS. 4 and 5, this section 22b is flat in collar shape.

According to a preferred and advantageous embodiment, the processing device 1 is such that, during processing, the container 3 is stationary. The pocket 6 is carried by its lower end portion 12 to the bottom 8 of the container 3. During the expansion of the volume of the pocket 6, resulting from which at least one product is gradually introduced into the pocket 6, the pocket 6 expands upward, held by the outside by the container 3. The upper end portion 13 of the pocket is therefore moved upward, while the lower end portion 12 remains at the same level. When the pocket 6 is emptied of its contents, the pocket 6 folds downward, in particular the upper end portion 13 is moved downward, whereby the lower end portion 12 remains at the same level. It is in reference to this preferred and advantageous embodiment and to these movements that the device 1 is described and that the expressions "upward" and "downward" should be understood in a conventional manner.

It is understood, however, that the movements are above all relative and that it is possible to consider that the upper end portion 13 of the pocket 6 remains at the same level, while the lower end portion 12 is moved upward or downward.

With reference being made to the preferred and advantageous embodiment described above, to movements that it induces, to the meaning to be given to the expressions "upward" and "downward," it appears that the movement of the upper end portion 13 of the pocket 6 upward or downward entrains a correlative movement of the protective means 7.

The arrangement of the mixing device 1 is such that the active inner portion 5 of the processing means 4 is essentially arranged in the inner space 23 of the protective means 7 when the pocket 6 is in the flat-folded state.

The peripheral portion of the inner space 23 of the protective means 7 around processing means 4, more specifically the active inner portion 5, forms a protective chamber 24, both the pocket 6 and processing means 4. The height of this protective chamber 24, counted along the axis 16, is H3.

Protection is understood as the fact, first of all, that the active inner portion 5 is prevented from interfering with the pocket 6, in particular the upper end portion 13, in the folded state and/or during the draining of the pocket 6, which prevents the constituent material of the pocket 6 from being embrittled, perforated or torn by the active inner portion 5, and the fact, then, that the active inner portion 5 is prevented from interfering with something rigid or in the case of impact, which prevents it from being altered more or less significantly, for example deformed or moved or else wedged.

The mixing means 4 (processing) and the protective means 7 are arranged to be independent of one another relative to their movements.

In the embodiment that is shown and described, the processing means 4 and the protective means 7 are dissociated structurally from one another, being separate from one another and without direct contact with one another. In this case, the peripheral portion of the inner space 23 of the protective means 7 around processing means 4 that form the protective chamber 24 extends laterally (horizontally) and on the top (vertically and upward) between the processing means 4, and, on the one hand, the side wall 21, and, on the other hand, the upper end portion 22, protective means 7.

In contrast, the height H3 of the protective chamber 24 is variable. It can be one of two extreme heights, maximum and minimum (and any intermediate height) based on the respectively flat-folded and unfolded, expanded states (and any intermediate state) of the pocket 6. In addition, the height H3 of the protective chamber 24 adapts automatically, based on the state of the pocket 6.

The constructive arrangements that are described are such that in each state of the pocket 6, the mixing means 4 (processing) are offset from the side wall 11 and the upper end portion 13 of the pocket 6, while being—and remaining—adjacent to its lower end portion 12.

In the flat-folded state of the pocket 6, the active inner portion 5 of the processing means 4 essentially occupies the inner space 23 of the protective means 7.

In the deployed state of the pocket 6, the active inner portion 5 of the processing means 4 is essentially integral in the inner space 14—then maximum—of the pocket 6, whereby the height H3 of the protective chamber 24 is minimum and zero.

During the refolding of the pocket 6, subsequent to its draining, the active inner portion 5 of the processing means 4 is rehoused in the inner space 23 of the protective means 7, which allows the implementation of the active portion, in particular its movement, up to the end of the draining of the pocket 6.

In the particular application where the processing is a mixing, the receptacle 2—mixing receptacle—comprises at least a second opening 25 for introducing a second portion of at least one product. This at least one second introduction opening 25 is provided in the upper end portion 22 of the protective means 7, being at the top, while the first introduction opening 18 is on the bottom. Thus, the protective means 7 form a head 26 for introducing at least one product into the receptacle 2, comprising, in addition to the at least one second opening 25, removable means 27 for sealing the second opening 25.

The removable sealing means 27 of the second opening 25 are capable of ensuring its closing and its opening.

In the embodiment that is shown in FIGS. 1 and 4, the removable means 27 for sealing the second opening 25 comprise a plug that is kept in place on a collar 28 that is provided on the free edge of the upper end portion 22 that forms a port that has a general chimney shape around the opening 25, based on a suitable holding system that is removable.

In the embodiment that is shown in FIG. 2, the removable means 27 for sealing the second opening 25 comprise a membrane that is secured by gluing or welding to the free edge of the upper end portion 22 in the general shape of a chimney. This membrane can be removed by peeling, in particular using a pull tab 29.

Of course, these removable sealing means 27 do not exclude other embodiments.

Further, the introduction head 26 can, in one embodiment, not shown, comprise removable means of the receptacle 2 for connection to an aseptic transfer device, of the type of those that comprise an aseptic transfer pocket.

Under these conditions, the mixing device 1 makes possible, according to the embodiments, an addition of product in an aseptic or non-aseptic manner.

The protective means 7 ensure in combination not only the function of protection of the pocket 6 and processing means 4, described above, but also a guiding function of the pocket 6, when, the opening 18 being open, the at least one product (arrow R in FIGS. 3 and 5) is gradually introduced into the receptacle 2, while simultaneously the pocket 6 expands upward, as well as during the draining of the pocket 6.

A first embodiment of the protective means 7 is now described with reference to FIGS. 1 to 3. In this first embodiment, the protective means 7—and in particular the side wall 20—are rigid and non-deformable. The protective means 7 then have a general shape that corresponds to a wide prism that is terminated by a collar at the low portion, a cylindrical chimney of smaller diameter in the top portion, and, between the two, a tapered portion.

A second embodiment of the protective means 7 is now described with reference to FIGS. 4 and 5. In this second embodiment, the protective means 7—and in particular the side wall 20—can be deformed in height.

In this second embodiment, the side wall 20 of the protective means 7 comprises at least one section 30 of a deformable portion between two extreme states, respectively flat-folded and expanded vertically, in contrast capable of being deformed to switch from one state to the other. If necessary, it is the entire side wall 20 that is deformable.

In addition to a suitable deformability of the deformable section 30, suitable means are provided that are capable of keeping the deformable section 30 expanded, when this is desired, in particular at least in the flat-folded extreme state of the pocket and in the absence of stress.

In one embodiment, such means that are capable of keeping the deformable section 30 expanded are integrated in the deformable section 30 and in the side wall 20 that is of the compressible type. This is defined as the deformable section 30 comprising peripheral ribs that in the absence of external stress are capable of keeping the deformable section expanded but that can, as a result of external compressive stress (support toward the bottom), become deformed such that the deformable section 30 folds like an accordion.

In another embodiment, in which the deformable section 30 is flexible, the means that are capable of keeping the deformable section 30 expanded are separate from the side wall 20. They can consist of a removable outside support, able to be carried itself by the container 3 toward its opening 10.

Further, being designed to be arranged in the container 3, the container 2 advantageously comprises means 31 that are capable of participating in its holding in the container 3, whereby the pocket 6 contains the desired amount of at least one product.

According to one embodiment, such means 31 are integrated or connected to protective means 7. They can consist of, for example, an outer collar that is provided on the outer surface of the side wall 20 of the protective means 7 toward the lower end portion 21. Such a collar 31 can then work with a conjugated portion that is provided for this purpose in the container 3, such as the collar return 10a. According to one embodiment, this conjugated portion comprises two removable crosspieces, mounted on the container 3, carried by and secured in a removable manner to the container 3 toward its upper opening and arranged under the collar 31 once the pocket 6 has been filled.

A processing receptacle 6 (mixing) as described above can be found in a storage situation before use. The pocket 6 that contains the active inner portion 5 of the processing means 4 is then in the folded state. In this state, the pocket 6 has minimal outside occupied space and can be easily stored and handled. It is understood that in this situation, the pocket 6 is closed, whereby the openings 18, 25 are sealed.

To implement the processing device 1 (mixing), such a receptacle 2 and a container 3 are used, whereby the two constitute the device 1. The pocket 6 of the receptacle in the flat-folded state is placed in the container 3, on the bottom 8. As indicated above, the active inner portion 5 of the processing means 4 then essentially occupies the inner space 23 of the protective means 7 by thus being offset from the side wall 11 and the upper end portion 13 of the pocket 6. The pocket 6 and the processing means 4 are thus protected (FIGS. 1, 2 and 4). The protective chamber 24 is then maximal.

The first opening 18 for introducing into the pocket 6 a first portion of at least one product to be mixed being open, a first portion of at least one product is gradually introduced into the mixing receptacle 2.

Simultaneously, the pocket 6 is allowed to expand upward and to be expanded in volume by the container 3.

The inner space 14 of the pocket 6 sees its volume increase gradually, accommodating the at least one product.

This stage is continued until having introduced the desired amount of at least one product into the container 2.

During this stage, the protective means 7 are allowed to move upward, being driven by the movement of the upper end portion 13 of the pocket 6.

Further, during this stage, and as the protective means 7 move upward, the height of the protective chamber 24 is allowed to decrease from the preceding maximum extreme height and to adapt automatically based on the state of the pocket 6 until the pocket 6 is in the unfolded and expanded state—or any intermediate state—based on the amount of product that is introduced into the pocket 6 (FIGS. 3 and 5). The active inner portion 5 of the processing means 4 is then completely freed from the protective chamber 24 to be located integrally in the inner space 14 of the pocket 6.

In the case of the second embodiment of the protective means 7, the deformable section 30 is, in the expanded state, at least at the beginning of the upward movement of the protective means 7. Once the pocket 6 is in the unfolded and expanded state, the deformable section 30 can be compressed. This constituent arrangement makes it possible to limit the upward occupied space of the device 1 and to house the latter integrally or almost integrally in the container 3. If necessary, the deformable section 30 is compressed as upward movement of the protective means 7 proceeds.

In all of the states of the pocket, the active inner portion 5 of the processing means 4 is offset from the side wall 11 and the upper end portion 13 of the pocket 6 while being—and remaining—adjacent to its lower end portion 12. The pocket 6 and the processing means 4 thus always remain protected by a type of permanent and modular protection screen between the pocket 6 and the active inner portion 5.

The process also comprises a stage in which the processing means 4 of at least one product that is in the receptacle 2 are implemented.

In the case where the processing is a mixing, a second portion of at least one product is introduced into the receptacle 2 by the second introduction opening 25 that is open for this purpose (arrow R, FIGS. 3 and 5). For example, a product in the solid state is introduced, while the receptacle 2 contains a product in the liquid state.

According to the embodiments, the introduction of the second portion of at least one product via the second introduction opening 25 begins when an adequate amount of the first portion of the product is found in the pocket 6, or when the entire first portion of the product has been introduced into the pocket 6.

According to the embodiments, the implementation of the mixing means 4 of at least one product that is found in the receptacle 2 is begun before, at the time of, or after the introduction of the desired amount of at least one product into the receptacle 2. And, the mixing means 4 are implemented while the at least one second introduction orifice 25 is open or closed.

As indicated above, it is understood that the movements should be considered as relative movements.

During the draining of the receptacle 2, the draining opening 18a that is provided for this purpose is opened. Contrary to the practice of the prior art, it is possible to drain the pocket 6 completely, without running the risk of tearing, using protective means 7 that form a screen. In addition, it is possible to continue the mixing until draining is complete, whereby the active portion 5 is protected, as has been described.

The mixing process therefore also has the optional characteristic that the mixing means 4 are implemented until draining of the pocket 6 is complete or essentially complete.

The invention claimed is:

1. A processing receptacle for at least one biopharmaceutical product, comprising:
   a pocket that has a flexible side wall, a lower end portion and an upper end portion that define a first inner space that is designed to accommodate the at least one product, wherein the pocket can be in two extreme states, flat-folded and expanded, and in any intermediate state, and can be deformed to switch from one state to the other;
   a processing means for processing said at least one biopharmaceutical product that is contained in the inner space of the pocket, comprising an active inner portion of a certain height that is arranged inside the receptacle;
   a protective means for protecting the processing means, comprising a side wall, a lower end portion and an upper end portion that define second inner space communicating with the first inner space of the pocket, the lower end portion of the protective means being adjacent and attached rigidly to the upper end portion of the pocket, movement of the upper end portion of the pocket upward or downward bringing about a movement of the protective means, whereby an active inner portion of the processing means is essentially arranged in the second inner space of the protective means when the pocket is in the flat-folded state, the peripheral portion of the second inner space of the protective means around the processing means forming a protective chamber of the pocket and the processing means; and
   at least one opening for introducing at least one product into the receptacle and/or for draining the contents from the receptacle;
   wherein:
   at least the active inner portion and the processing means are arranged inside the pocket by being adjacent to its lower end portion;
   the processing means and the protective means are arranged to be independent from one another relative to their movements;
   the variable height of the protective chamber can be one of two extreme heights, maximum and minimum, and any intermediate height, and can be adapted automatically, based on the state that is respectively flat-folded, unfolded and expanded, and any intermediate state of the pocket;
   in each state of the pocket, the processing means is offset from the side wall and the upper end portion of the pocket, while being adjacent to its lower end portion; and
   the protective means is deformable in height, whereby the side wall comprises at least one deformable section between two extreme states, respectively folded and expanded, that is capable of being deformed to switch from one state to another, and the receptacle comprises means for keeping the deformable section expanded, at least in the flat-folded extreme state of the pocket.

2. The processing receptacle according to claim 1, wherein the means for keeping the deformable section expanded, at least in the flat-folded extreme state of the pocket, is integrated in the side wall of the protective means or is separate therefrom.

3. The processing receptacle according to claim 1, wherein the protective means is arranged to form a head configured to introduce at least one product into the receptacle.

4. The processing receptacle according to claim 3, wherein the protective means that forms the head comprises at least one opening configured to introduce said at least one product, the opening being provided in the upper end portion of the protective means, and a removable means for sealing said opening that is capable of ensuring its closing and its opening.

5. The processing receptacle according to claim 3, wherein the head comprises a means for removably connecting the receptacle to an aseptic transfer device.

6. The processing receptacle according to claim 1, comprising at least one opening configured to introduce at least one product into the receptacle and/or to drain the contents provided in the pocket from the receptacle.

7. The processing receptacle according to claim 6, comprising at least one opening configured to introduce at least one product into the receptacle and/or to drain the contents provided in the lower end portion of the pocket from the receptacle.

8. The processing receptacle according to claim 1, wherein the pocket comprises a rigid plate on its lower end portion.

9. The processing receptacle according to claim 1, wherein the means for protecting the processing means, in combination a protective function of the pocket, the processing means and a guiding function of the pocket, is configured so that when the opening is open, the at least one product is gradually introduced into the receptacle, while simultaneously the pocket expands upward.

10. The processing receptacle according to claim 1,
    wherein the processing means and the protective means are dissociated structurally from one another, being separate from one another and without direct contact between them,
    whereby the peripheral portion of the inner space of the protective means around said processing means forms a protective chamber that extends laterally and on the top between the processing means and the side wall and the upper end portion of the protective means.

11. The processing receptacle according to claim 1, wherein the processing means comprises an active portion inside the pocket that, in the flat-folded state of the pocket, essentially occupies the inner space of the protective means.

12. The processing receptacle according to claim 1, wherein the processing means comprises an active portion inside the pocket that, in the expanded state of the pocket, is essentially integral in the inner space of the pocket, whereby the minimum height of the protective chamber is zero.

13. The processing receptacle according to claim 1, wherein the processing means comprises an active portion inside the pocket, if necessary with the possibility of relative movement, an inner surface of the lower end portion of the pocket or by a rigid plate that equips the lower end portion of the pocket on the inside.

14. A device for processing at least one biopharmaceutical product, comprising the receptacle according to claim 1, and
    a rigid container configured to accommodate the receptacle when the pocket is in the flat-folded state, the expanded state, or in an intermediate state, to allow the pocket to be deformed in order to switch from one state to the other, and to guide the pocket so that the pocket is expanded in volume, with an additional volume of that of the container, when the at least one product is introduced into the receptacle.

15. A method for processing a biopharmaceutical product, comprising:
    providing a device, the device comprising:
    (i) a processing receptacle, comprising:
    a pocket that has a flexible side wall, a lower end portion and an upper end portion that define a first inner space that is designed to accommodate the at least one product, wherein the pocket can be in two extreme states, flat-folded and expanded, and in any intermediate state, and can be deformed to switch from one state to the other;

a processing means for processing said at least one biopharmaceutical product that is contained in the inner space of the pocket, comprising an active inner portion of a certain height that is arranged inside the receptacle;

a protective means for protecting the processing means, comprising a side wall, a lower end portion and an upper end portion that define second inner space communicating with the first inner space of the pocket, the lower end portion of the protective means being adjacent and attached rigidly to the upper end portion of the pocket, movement of the upper end portion of the pocket upward or downward bringing about a movement of the protective means, whereby an active inner portion of the processing means is essentially arranged in the second inner space of the protective means when the pocket is in the flat-folded state, the peripheral portion of the second inner space of the protective means around the processing means forming a protective chamber of the pocket and the processing means; and at least one opening for introducing at least one product into the receptacle and/or for draining the contents from the receptacle; wherein, at least the active inner portion and the processing means are arranged inside the pocket by being adjacent to its lower end portion, the processing means and the protective means are arranged to be independent from one another relative to their movements, the variable height of the protective chamber can be one of two extreme heights, maximum and minimum, and any intermediate height, and can be adapted automatically, based on the state that is respectively flat-folded, unfolded and expanded, and any intermediate state of the pocket, in each state of the pocket, the processing means is offset from the side wall and the upper end portion of the pocket, while being adjacent to its lower end portion, and the protective means is deformable in height, whereby the side wall comprises at least one deformable section between two extreme states, respectively folded and expanded, that is capable of being deformed to switch from one state to another, and the receptacle comprises means for keeping the deformable section expanded, at least in the flat-folded extreme state of the pocket; and (ii) a rigid container configured to accommodate the receptacle when the pocket is in the flat-folded state, the expanded state, or in an intermediate state, to allow the pocket to be deformed in order to switch from one state to the other, and to guide the pocket so that the pocket is expanded in volume, with an additional volume of that of the container, when the at least one product is introduced into the receptacle;

placing the pocket of the receptacle in the flat-folded state on the bottom of the container;

gradually introducing through said at least one opening the at least one biopharmaceutical product into the receptacle and simultaneously allowing the pocket to expand upward and to be expanded in volume by the container, the inner space of the pocket of increasing volume accommodating the at least one product;

continuing this stage until having introduced the desired amount of the at least one product into the receptacle;

allowing the protective means to move upward, the movement being entrained by the movement of the upper end portion of the pocket;

allowing the height of the protective chamber to decrease, starting from the maximum extreme height and automatically adapting based on the state of the pocket until the pocket is in the unfolded and expanded state or any intermediate state, based on the amount of product that is introduced into the receptacle, such that in all of the states of the pocket the processing means is offset from the side wall and the upper end portion of the pocket, while being adjacent to the lower end portion; and implementing the processing means of at the least one product that is in the receptacle.

16. The process according to claim 15, wherein implementing the processing means of at the least one product in the receptacle is begun before, at the time of, or after introducing the desired amount of the at least one product into the receptacle.

17. The process according to claim 15, wherein
the receptacle comprises a first opening for introducing a first portion of the at least one product into the receptacle, and a second opening for introducing a second portion of the at least one product, the second opening provided in the upper end portion of the protective means, the second opening being sealed; the process comprising:

placing the pocket of the receptacle in the flat-folded state on the bottom of the container;

introducing a first portion of the at least one product into the mixing receptacle via a first introduction opening;

introducing a second portion of the at least one product into the receptacle via a second introduction opening.

18. The process according to claim 17, further comprising implementing a means for mixing, while the second introduction opening is open or closed.

19. The process according to claim 17, wherein the mixing means is implemented until the pocket is completely or essentially completely drained.

20. A processing receptacle for at least one biopharmaceutical product, comprising:

a pocket that has a flexible side wall, a lower end portion and an upper end portion that define a first inner space that is designed to accommodate the at least one product, wherein the pocket can be in two extreme states, flat-folded and expanded, and in any intermediate state, and can be deformed to switch from one state to the other;

a processing means for processing said at least one biopharmaceutical product that is contained in the inner space of the pocket, comprising an active inner portion of a certain height that is arranged inside the receptacle;

a protective means for protecting the processing means, comprising a side wall, a lower end portion and an upper end portion that define second inner space communicating with the first inner space of the pocket, the lower end portion of the protective means being adjacent and attached rigidly to the upper end portion of the pocket, movement of the upper end portion of the pocket upward or downward bringing about a movement of the protective means, whereby an active inner portion of the processing means is essentially arranged in the second inner space of the protective means when the pocket is in the flat-folded state, the peripheral portion of the second inner space of the protective means around the processing means forming a protective chamber of the pocket and the processing means; and at least one opening for introducing at least one product into the receptacle and/or for draining the contents from the receptacle;

wherein, at least the active inner portion and the processing means are arranged inside the pocket by being adjacent to its lower end portion;

the processing means and the protective means are arranged to be independent from one another relative to their movements;

the variable height of the protective chamber can be one of two extreme heights, maximum and minimum, and any intermediate height, and can be adapted automatically, based on the state that is respectively flat-folded, unfolded and expanded, and any intermediate state of the pocket;

in each state of the pocket, the processing means is offset from the side wall and the upper end portion of the pocket, while being adjacent to its lower end portion; and the protective means is arranged to form a head configured to introduce at least one product into the receptacle, and comprises at least one opening provided in the upper end portion of the protective means, and a removable means for sealing said opening that is capable of ensuring its closing and its opening.

21. The processing receptacle according to claim 20, wherein the removable sealing means is a plug or a membrane.

22. A processing receptacle for at least one biopharmaceutical product, comprising:

a pocket that has a flexible side wall, a lower end portion and an upper end portion that define a first inner space that is designed to accommodate the at least one product, wherein the pocket can be in two extreme states, flat-folded and expanded, and in any intermediate state, and can be deformed to switch from one state to the other;

a processing means for processing said at least one biopharmaceutical product that is contained in the inner space of the pocket, comprising an active inner portion of a certain height that is arranged inside the receptacle;

a protective means for protecting the processing means, comprising a side wall, a lower end portion and an upper end portion that define second inner space communicating with the first inner space of the pocket, the lower end portion of the protective means being adjacent and attached rigidly to the upper end portion of the pocket, movement of the upper end portion of the pocket upward or downward bringing about a movement of the protective means, whereby an active inner portion of the processing means is essentially arranged in the second inner space of the protective means when the pocket is in the flat-folded state, the peripheral portion of the second inner space of the protective means around the processing means forming a protective chamber of the pocket and the processing means; and at least one opening for introducing at least one product into the receptacle and/or for draining the contents from the receptacle;

wherein, at least the active inner portion and the processing means are arranged inside the pocket by being adjacent to its lower end portion;

the processing means and the protective means are arranged to be independent from one another relative to their movements;

the variable height of the protective chamber can be one of two extreme heights, maximum and minimum, and any intermediate height, and can be adapted automatically, based on the state that is respectively flat-folded, unfolded and expanded, and any intermediate state of the pocket;

in each state of the pocket, the processing means is offset from the side wall and the upper end portion of the pocket, while being adjacent to its lower end portion; and the protective means is arranged to form a head configured to introduce at least one product into the receptacle, and the head comprises a means for removably connecting the receptacle to an aseptic transfer device.

* * * * *